(12) United States Patent
Karell

(10) Patent No.: US 6,430,443 B1
(45) Date of Patent: Aug. 6, 2002

(54) METHOD AND APPARATUS FOR TREATING AUDITORY HALLUCINATIONS

(76) Inventor: Manuel L. Karell, 3573 —22 St., San Francisco, CA (US) 94114

( * ) Notice: Subject to any disclaimer, the term of this patent is extended or adjusted under 35 U.S.C. 154(b) by 0 days.

(21) Appl. No.: 09/551,154

(22) Filed: Mar. 21, 2000

Related U.S. Application Data

(63) Continuation-in-part of application No. 08/899,472, filed on Mar. 21, 2000, now abandoned.

(51) Int. Cl.⁷ .................................................. A61N 1/32
(52) U.S. Cl. .......................................... 607/55; 607/57
(58) Field of Search ......................... 607/2, 3, 45, 46, 607/55–58, 72–76

(56) References Cited

U.S. PATENT DOCUMENTS

| | | |
|---|---|---|
| 4,702,254 A | 10/1987 | Zabara |
| 4,867,164 A | 9/1989 | Zabara |
| 4,988,333 A | 1/1991 | Engebretson |
| 5,025,807 A | 6/1991 | Zabara |
| 5,231,988 A | 8/1993 | Wernicke |
| 5,269,303 A | 12/1993 | Wernicke |
| 5,299,569 A | 4/1994 | Wernicke |
| 5,540,734 A | 7/1996 | Zabara |
| 5,549,658 A | 8/1996 | Shannon |
| 5,975,085 A | 11/1999 | Rise |

Primary Examiner—Jeffrey R. Jastrzab

(57) ABSTRACT

Stimulating one or more vestibulocochlear nerves or cochlea or cochlear regions will treat, prevent and control auditory hallucinations.

23 Claims, 11 Drawing Sheets

METHOD AND APPARATUS FOR TREATING AUDITORY HALLUCINATIONS

This is a C.I.P application of application Ser. No. 08/899,472 filing date Jul. 23, 1997 now abandoned.

FIELD OF THE INVENTION

The present invention generally relates to method and apparatus for treating, controlling or preventing auditory hallucinations by the application of modulating electrical signals to a vestibulocochlear cranial nerve or cochlea or cochlear region and/or by the application of audio signals through an ear.

BACKGROUND OF THE INVENTION

Scientific advances have revealed that schizophrenia is primarily organic and not psychological in nature. Scrambled language, distorted thoughts, and auditory hallucinations are the hallmarks of schizophrenia and have been linked to abnormal physical changes in specific areas of the human brain that begin during pregnancy. Auditory hallucinations are a prominent symptom and present in nearly all schizophrenic patients. Hallucinations are defined as sensory perceptions without environmental stimuli and occur as simple experiences of hearing, tasting, smelling, touching, or seeing what is not physically present; they also occur as mixed or complex experiences of more than one simple experience. When these experiences take the form of "voices" arising internally, the subjective experience is of "hearing" the voice of another, an auditory hallucination.

Theories of the etiology of hallucinations include (1) stimulation and/or (2) inhibition. Examples of stimulation are neurochemical (for example, the neurotransmitter dopamine) changes, electrical discharges, and seizure episodes. An example of inhibition causing an hallucination is when there is destruction of normally inhibitory functions, resulting in disinhibition, as in the phantom limb syndrome. Auditory hallucinations arising from the disordered monitoring of inner speech (thinking in words) may be mixed stimulation and inhibition. Other theories of the etiology of schizophrenia include infection, autoimmune or immune dysfunction, and environmental.

Hallucinations occur in a wide range of human experiences. For example, there are physician prescribed medications known to cause hallucinations; and there are drugs of abuse such as alcohol and LSD that are also known to cause hallucinations. Auditory hallucinations may occur in organic brain disorders such as epilepsy, Parkinson's and Alzheimer's disease. Hallucinations may occur to bilingual schizophrenics; for example, they can be perceived in English even though his/her mother tongue may be Spanish.

Hearing impairment (acute or chronic) combined with stress may lead to pseudo-hallucinations in normal persons. Auditory hallucinations may occur in diseases not involving the brain, such as otosclerosis (where the bones in the ear do not move freely); in this case the auditory hallucinations may be cured with surgery.

The brain activity of schizophrenics who hear imaginary voices has been found to be similar to the brain activity of people that are hearing real voices. Schizophrenia may be the result of dysfunction of neurons utilizing dopamine as a neurotransmitter; the antipsychotic (neuroleptic) drugs block dopamine. Auditory hallucinations found in disorders such as schizophrenia are associated with an abnormal pattern of brain activation, as can be seen with brain imaging, such as positron emission tomography (PET), and by other means, such as encephalographic methods.

Auditory hallucinations involve language regions of the cortex in a pattern similar to that seen in normal subjects listening to their own voices but different in that left prefrontal regions are not activated. The striatum plays a critical role in auditory hallucinations. Magnetic resonance imaging (MRI) has shown that the hippocampal-amygdala complex and the parahippocampal gyrus (areas in the temporal lobe) are reduced in schizophrenic patients. Schizophrenics have increased levels of dopamine in the left amygdala. When using functional MRI brain imaging, a patient is positioned within an imaging apparatus; protons within the brain are then made to radiate a signal, which can be picked up with a radio antenna. Active areas of the brain will radiate a different signal than areas of the brain that are at rest; scanning schizophrenics while they are hallucinating is possible.

Magnetic resonance spectroscopy has found that schizophrenic patients have lower levels of several nucleic acids in the brain, including phosphomonoesters and inorganic phosphate and higher levels of phosphodiesters and adenosine triphosphate. Neurotransmitters such as dopamine, serotonin (5-HT), norepinephrine and glutamates are involved. It has been postulated that loss of input to the prefrontal cortex results in lack of feedback to other circuits of the limbic regions which leads to hyperactivity of the dopamine pathways.

Computed tomography (CT) studies have repeatedly shown that the brains of schizophrenic patients have lateral and third ventricular enlargement and some degree of reduction in cortical volume. Other CT studies have reported abnormal cerebral asymmetry, reduced cerebellar volume, and brain density changes.

Changes in the bioelectrical brain activity are recorded in electroencephalography (EEG). The changes for schizophrenic patients are: (1) "choppy activity"—prominent low voltage, with desynchronized fast activity—considered as highly specific for schizophrenia; (2) intermittent occurrence of slow, high amplitude waves; (3) waves most prominent in the frontal region for delta, and in the occipital region for the theta; (4) pattern of increased slow activity; (5) decrease in alpha peak frequencies; (6) increased beta power; (7) increased left frontal delta power; (8) more anterior and superficial equivalent-dipoles in the beta bands. Some EEG changes are best noted during transition from wake to sleep.

In general, there are three changes in the EEG recordings: (i) spontaneous EEG, (ii) Event-Related Potentials and (iii) event-related EEG changes known as Event-Related Desynchronization and Event-Related Synchronization. Both real and imagined movement and both real and imagined voices may cause changes in these three types of EEG recording.

Hallucinations effect evoked potentials and alpha frequency which are noted when using quantitative EEG (qEEG).

Normal brain structures related to language tend to be larger on the left side; however, schizophrenic patients have the asymmetry reversed. Persons who have epilepsy of the left temporal lobe of the brain exhibit symptoms resembling schizophrenia. The brain activity of schizophrenics who hear imaginary voices has been found to be similar to the brain activity of people that are hearing real voices; however, the initiation of this brain activity arises from within rather than from external sources.

The planum temporale is associated with comprehending language, and if one stimulates this area electrically, a person hears complex sounds similar to a schizophrenic's auditory hallucinations.

Recognized in the prior art are methods and apparatus for treating and controlling medical disorders, psychiatric disorders, or neurological disorders, by applying modulating electrical signals to a selected nerve of a patient. For example, in U.S. Pat. No. 5,540,734 to Zabara, 1996, the patient's trigeminal and glossopharyngeal nerves are used, and in U.S. Pat. No. 5,299,569, to Wernicke, 1994 the vagus nerve is used U.S. Pat. No. 5,975,085 issued to Rise, 1999 discusses a method of treating schizophrenia by brain stimulation and drug infusion using an implantable signal generator and electrode and an implantable pump and catheter. A catheter is surgically implanted in the brain to infuse the drugs, and one or more electrodes are surgically implanted in the brain to provide electrical stimulation.

Cochlear implants for deaf individuals are recognized in the art. For example, U.S. Pat. No. 4,988,333 to Engebretson, 1991, and U.S. Pat. No. 5,549,658 to Shannon, 1996 describe how audiologic signals are converted into electrical signals for stimulating a cochlea or cochlear region for conducting to a vestibulocochlear nerve for simulating speech to a deaf individual. The electrical stimulations supplied by the cochlear implant give rise to ascending electrochemical activities reaching the cortex. These activities can be sensed and recorded, for example, with scalp electrodes by evoked potentials or fields techniques. Persons who have had cochlear implants show nerve, neurochemical, and brain function closely comparable to the responses of normal hearing people. For example, both normal hearing and cochlear implant individuals show similar neuronal metabolism's increase which is associated with a cerebral blood flow increase. Single photon or PET and functional MRI demonstrate increased blood flow changes associated with an auditory stimulation and during auditory hallucinations.

The prior art fails to recognize that stimulation of at least one of a patient's vestibulocochlear nerves, cochlea or cochlear regions with or without cochlear implant, can provide the therapeutic treatments according to the instant invention.

The prior art fails to recognize that auditory stimulation, both supra- and sub-hearing as well as hearing frequencies, of at least one of a patient's ears with or without bone conduction can provide the therapeutic treatments according to the instant invention.

One theory is that auditory hallucinations occur because of abnormal brain activation. Stimulation to the vestibulocochlear nerve or cochlea or cochlear region or the combination thereof, causes brain activation similar to normal hearing brain activation. This normal hearing brain activation blocks hallucinatory activation similar to pacer electrical stimulation to the heart blocking abnormal internal electrical discharges. Stimulation may occur without monitoring, in a pulsed or continuous fashion. Stimulation may be patient controlled. Or upon monitoring, for example by qEEG, for early detection of an abnormal brain activation, a signal can be sent through a cochlea or cochlear region or vestibulocochlear nerve for inducing natural brain activation, thereby blocking abnormal brain activation producing auditory hallucinations. Blocking may be done in such a manner as to allow normal auditory speech to proceed and therefore normal brain processing of information, and thereby improve a patient's quality of life. Sounds beyond normal hearing, low frequency tones and/or high frequency tones, may accomplish such blocking. Out of hearing range tones may be converted to modulating electrical signal stimulation of a cochlea or cochlear region or a vestibulocochlear nerve.

Monitoring is usually performed with electrodes. However, monitoring may also be performed with a variety of sensors: implanted electrode sensors; and for example, sensors to pick up the presence of certain chemicals, which may then have a corresponding conversion to electrical impulses. EEG monitoring may be performed, for example, by a patient wearing a multi-electrode scalp hat and changes may be analyzed by a logic circuit means; upon detection of changes consistent with auditory hallucinations, a stimulating current may then be applied qEEG signal processing permits measuring and quantifying multiple aspects of brain electrical activity providing objective, precise information. qEEG provides objective numerical data that can be used for graphical display and for mathematical statistical analysis. The brain voltage fluctuations are digitally converted and compared. There are many signal processing techniques used in qEEG. Distinctive patterns of electrophysiologic abnormalities are now recognized: schizophrenic patients, depressed patients, demented patients, chronic alcoholics, obsessive-compulsive disorders, attention deficit disorders and others. These techniques may be used to actively monitor schizophrenics for hallucinations and to cause a modulated electrical stimulation through electrodes affixed to a vestibulocochlear nerve or cochlea or cochlear region.

SUMMARY OF THE INVENTION

An abnormal brain activation inducing auditory hallucinations may be blocked by applying modulating electrical signal stimulation of a vestibulocochlear cranial nerve or cochlea or cochlear region.

An abnormal brain activation inducing auditory hallucinations may be blocked by applying sound, audible and inaudible, with or without bone conduction to an ear.

An object of the invention is directed to methods of treating, controlling or preventing auditory hallucinations by application of modulating electrical signals directly to at least one of a patient's vestibulocochlear nerves, or cochlea or cochlear regions such as the middle ear.

An additional object of the invention is directed to methods of and apparatus for treating, controlling or preventing auditory hallucinations through use of the brain's natural mechanisms by application of audio signals to at least one ear inducing natural neuron excitation in at least one of a patient's vestibulocochlear nerves. Sounds beyond normal hearing range, that of sub-low frequency or that of high-ultrasound frequencies, may be modulated to induce nerve excitation which will block auditory hallucinations.

An additional object of the invention is to have cochlear implant technology applied to treat patient's having disorders with auditory hallucinations.

An additional object of the invention is to have newly developed techniques of picking up brain activity and monitoring used as a means to detect early audio hallucinations; once detected, to modulate an output signal from a stimulus generator applied to an vestibulocochlear nerve for blocking, controlling or preventing auditory hallucinations.

An additional object of the invention is to have new techniques of monitoring and picking up brain activity used as a means to detect early audio hallucinations and once detected, to modulate an output signal from a stimulus generator applied to a cochlea or cochlear region for blocking, controlling or preventing auditory hallucinations.

An additional object of the invention is that the patient may selectively and manually activate the stimulator or audio input to consciously control his/her auditory hallucinations. The patient may control all parameters of stimulation: frequency, amplitude, wave shape, duration, intermittent or constant.

BRIEF DESCRIPTION OF THE DRAWINGS

The foregoing summary, as well as the following detailed description of the preferred embodiment of the invention, will be better understood when read in conjunction with the appended drawings. For the purpose of illustrating the invention, there is shown in the drawing an embodiment which is presently preferred. It should be understood, however, that the invention is not limited to the precise arrangements and instrumentalities shown. In the drawings.

DETAILED DESCRIPTION OF PREFERRED EMBODIMENTS

One of the central nervous system's twelve cranial nerves is nerve eight called the vestibulocochlear nerve. The prior art fails to recognize that stimulation of at least one of a patient's vestibulocochlear nerves and/or cochlea and/or cochlear regions can provide the therapeutic treatments according to the instant invention. Recent studies of the brains of hallucinating patients show that it is possible for there to be reduced brain activation in the left middle temporal gyrus and the rostral supplementary motor area when imagining sentences spoken from another person's voice. The theory is that modulated stimulation of a vestibulocochlear nerve and/or cochlea or cochlear region may induce natural brain activation blocking abnormal changes.

Figure 1:
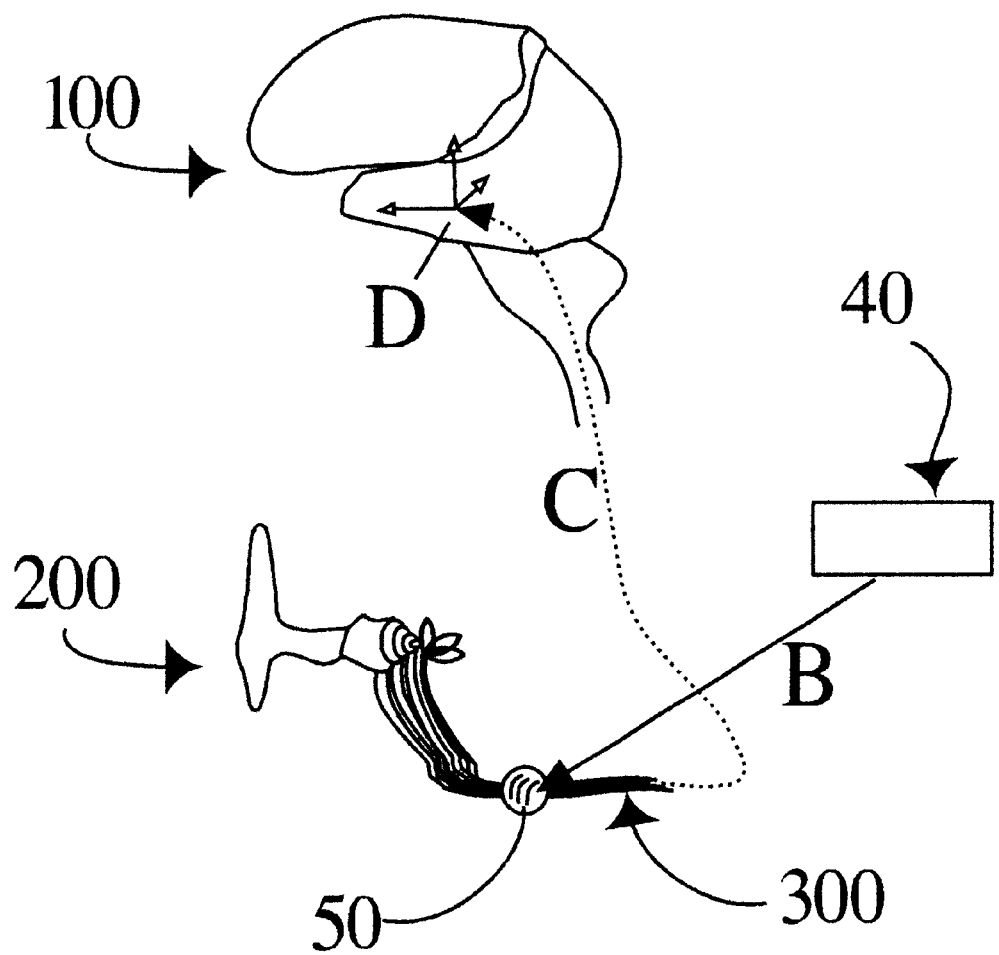
FIG. 1 is a schematic diagram illustrating a stimulator-electrode adapted to be affixed to a vestibulocochlear nerve from an ear which upon being energized causes neuro-impulses to reach a brain thereby causing normal brain activation impulses to spread.
Figure 2:
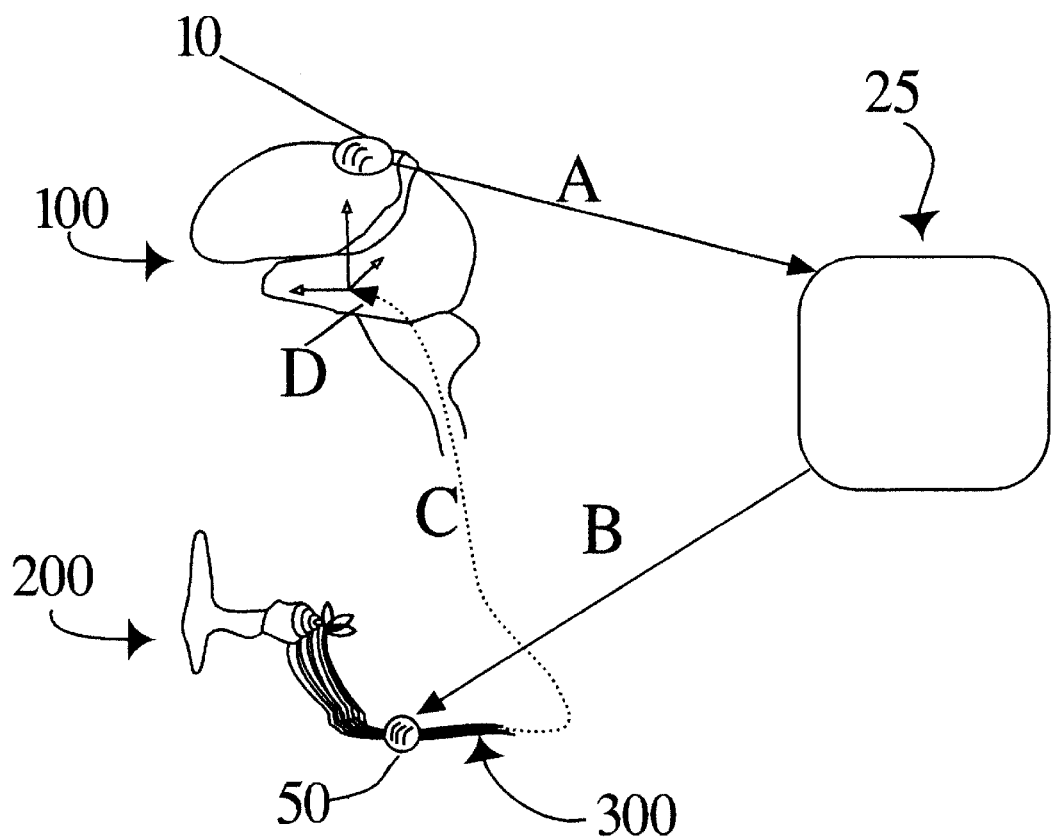
FIG. 2 is a schematic diagram illustrating a monitored brain sending signals to a controller which then sends signals to a vestibulocochlear nerve from an ear which causes normal brain activation.

The instant invention employs one or more electrodes adapted to be affixed to at least one of the vestibulocochlear nerves or cochlea or cochlear regions as illustrated in FIGS. 1 and 2. The following numerals refer to anatomical structures: 100 refers to a user's brain; 200 refers to a user's ear; 300 refers to a user's vestibulocochlear nerve. In the drawings, the ear and brain have been distanced for clarity. Neuro-impulses travel from the vestibulocochlear nerve to the brain through defined pathways and then spread to (activate) other regions of the brain. FIG. 1 shows schematically the method and apparatus whereby signal generator (40) sends signal(B) to stimulator-electrode(50) which has been adapted to be affixed to a vestibulocochlear nerve(300) from an ear(200); when stimulator-electrode(50) is energized, neuro-impulses(C) travel to brain(100) whereupon brain activation(D) then spreads throughout the brain. Signal generator(40), is well known in the art. In operation of this method and apparatus, an individual suffering from auditory hallucinations may have a switch to manually turn on the stimulation. Or an automatic switching means may be utilized. The signal generator(40) may output varying stimulations utilizing varying forms of wave shapes, duration, amplitude, frequency, pulse, intermittent, or constant stimulations. These various modalities can be manually controlled or not. One or more stimulator-electrodes may be utilized, which may be individually connected or bundled. Electrodes may be combined with other devices, for example, infusion pumps. The stimulator or signal generator may be implanted into the body, for example, subcutaneously; or it may be outside the body.

FIG. 2 shows schematically the method and apparatus additionally having the step of monitoring a patient's brain and then energizing a stimulator-electrode(50). A monitored brain activation signal(A) is input to the controller means (25). An output signal(B) is then sent to the stimulator-electrode(50). More specifically, a monitor-electrode(10) is adapted to be affixed to a brain(100) for detecting a brain activation; on detecting brain activation a first signal(A) is sent to a controller means(25). If an abnormal brain activation is present (hallucinations) then controller means(25) will in turn send a signal(B) to a stimulator-electrode(50) which has been adapted to be affixed to a vestibulocochlear nerve; on energizing the stimulator-electrode(50) neuron excitation is induced which causes a neuro-impulse signal (C) to travel by defined pathways to the brain which in turn causes normal brain activation to occur, represented by cluster of arrows(D); finally, the normal brain activation(D) inhibits the abnormal brain activation, thereby blocking auditory hallucinations. The cycle repeats wherein signal(A) now being sent is normal brain activation and thus controller (25) is not initiating electrical stimulation. Monitoring electrodes may be ion selective coated for directly transducing the amount of a particular transmitter substance or its breakdown by-products, indicating the relative activity of the particular brain region.

Figure 3:
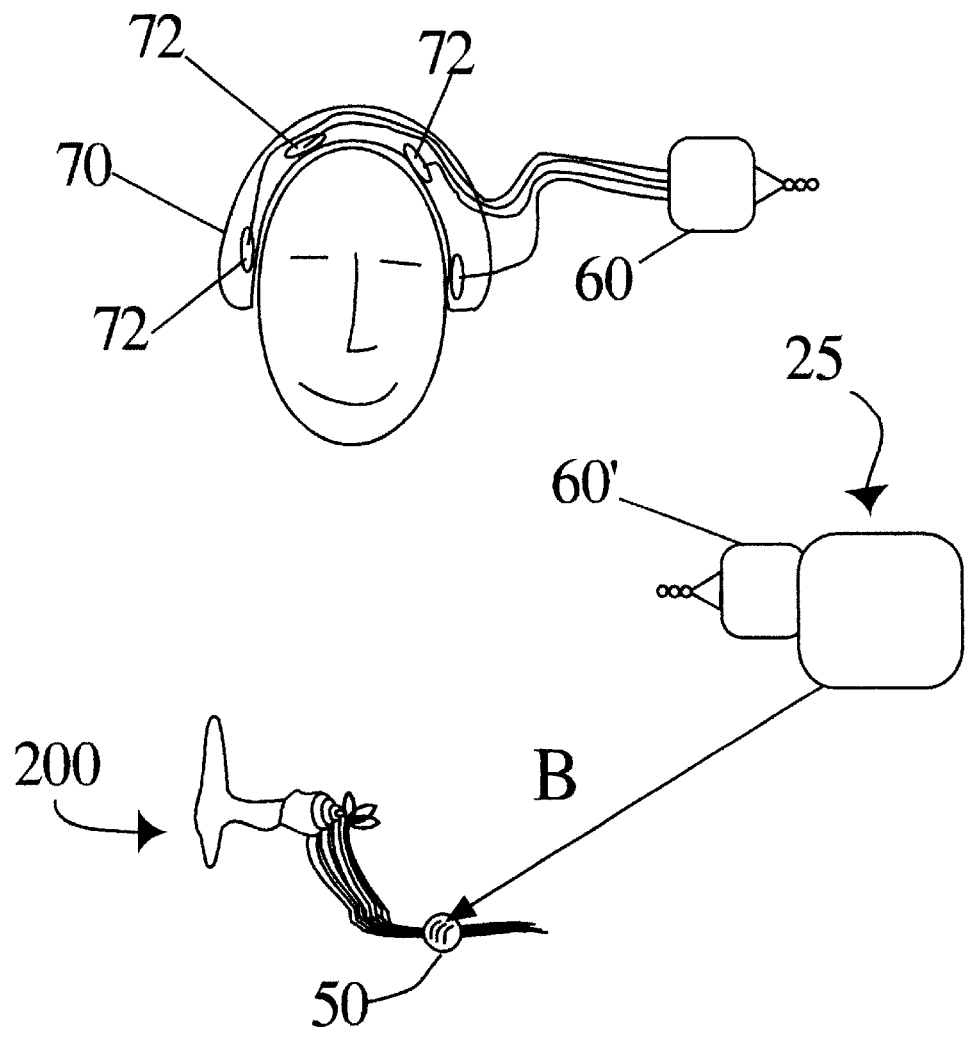
FIG. 3 is a schematic diagram illustrating a monitoring skull cap transmitting signals from a brain to a controller in turn causes neuro-impulses to occur.

One or more monitor-electrodes may be placed into the brain, or onto the brain or onto the skull. A transmitter means may be incorporated as in FIG. 3 for example, a skull cap(70) containing one or more monitor-electrodes(72) picks up brain activation and transmits signals via a transmitter/receiver(60) to another transmitter/receiver(60') operatively connected to controller(25); then controller(25) sends signal(B) to stimulator-electrode(50) for neuro-impulses to travel via defined pathways to the brain. Other varieties of sensors (other than electrodes) may be used to monitor brain activity and suitable for detecting symptoms of a disorder being treated. For example, a sensor for picking up the presence of a specific chemical may be utilized, and then converted to electrical signals. One or more monitor-electrodes may be utilized, which may be individually connected or bundled. Electrodes may be combined with other devices, for example, infusion pumps. The controller may be implanted into the body, for example, subcutaneously; or it may be outside the body. There may be transmission between an internally placed monitor and an externally placed controller. An implanted electrode has a proximal end coupled to the signal generator while having a stimulation portion stimulating the vestibulocochlear nerve, or cochlea or cochlear region.

Figure 4:
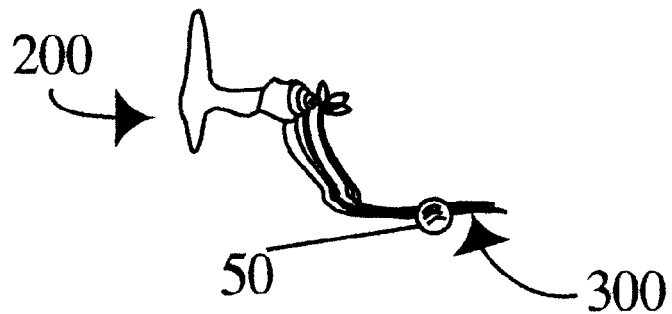
FIGS. 4, 4A, 4B schematically show different placements of stimulator-electrodes namely, vestibulocochlear nerve, vestibulocochlear region, and cochlea.
Figure 4A:
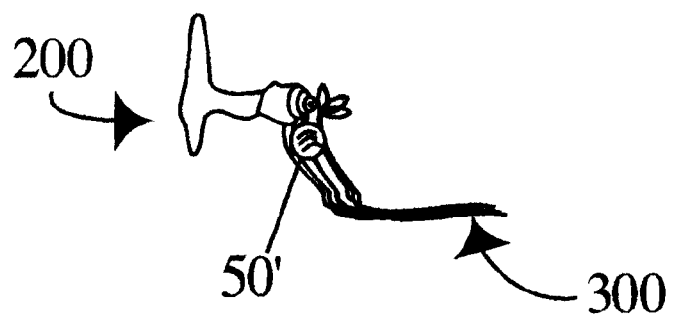
Figure 4B:
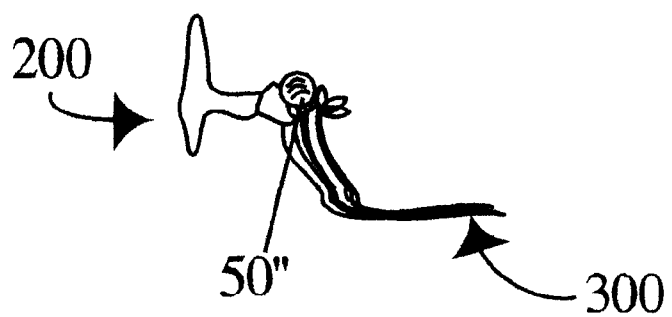

FIGS. 4, 4A, 4B show schematically differently positioned stimulator-electrodes (50, 50',50") on vestibulocochlear nerve, cochlear region, and cochlea respectively. It is possible to selectively stimulate the fibers of the cochlear or the vestibular components of the vestibulocochlear nerve.

Figure 5:
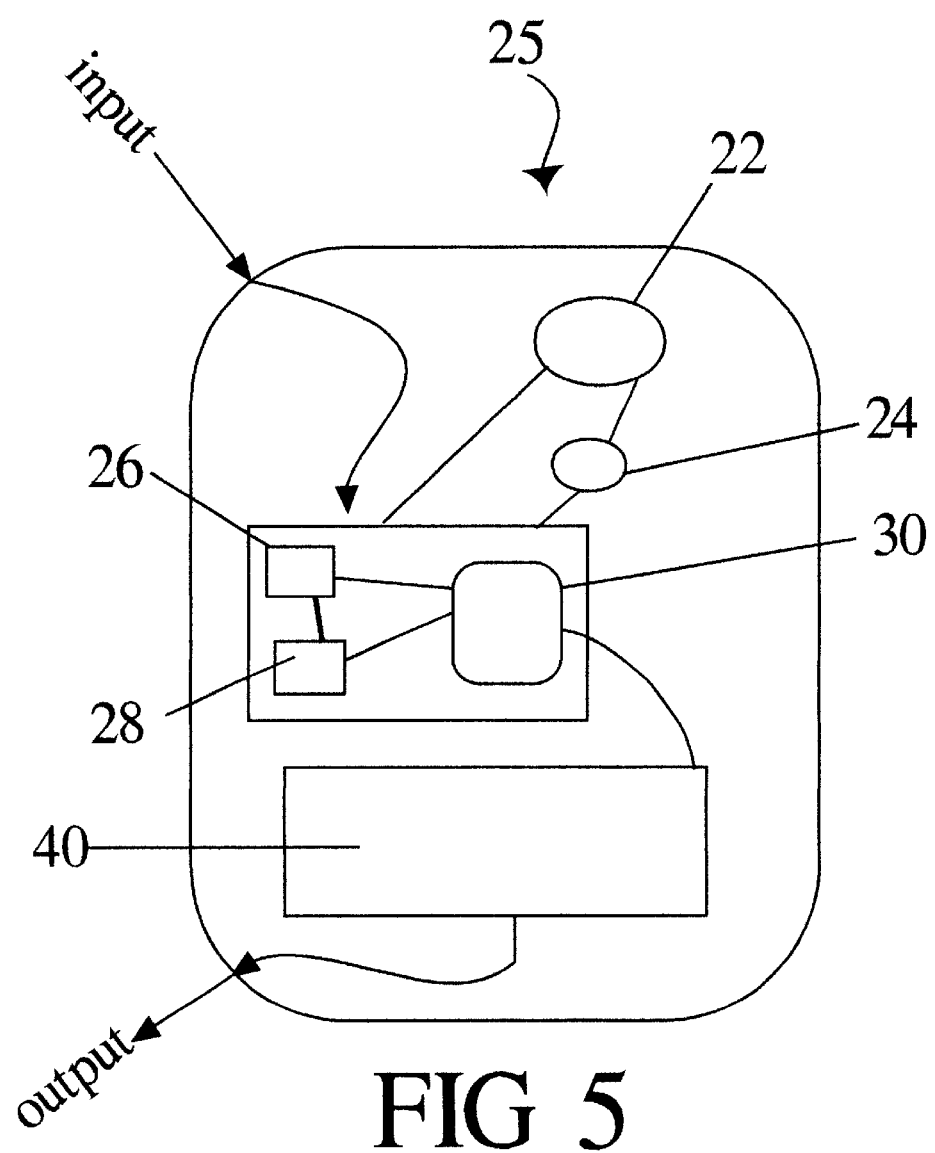
FIG. 5 schematically illustrates the input and output through a controller having a energy source, switching, comparer, logic, modulator, and signal generator means.

FIG. 5 shows schematically an enlargement of controller means(25) having input and output. Controller means(25) has an energy means(22) and a switching means(24). Additionally, controller means(25) is composed of a comparer means(26), a logic means(28), a modulator means(30) and a signal generator(40).

In operation, a signal coming from the brain is input to controller mean(25), whereupon a determination is made that an abnormal brain activation is present; thereafter, a modulated stimulus is output to a vestibulocochlear nerve. The input signal goes to comparer means(26) for comparison to predetermined parameters; then logic means(28) determines if an abnormal brain activation (hallucination) is present. If present, the modulator means(30) causes signal generator means(40) to output a signal. The output signal goes to stimulator-electrode(50) which causes neuro-impulses to activate the brain. Any or all of the components of the controller may be internal or external to the body. Wireless transmission may be utilized for local or telemedicine applications.

Figure 6:
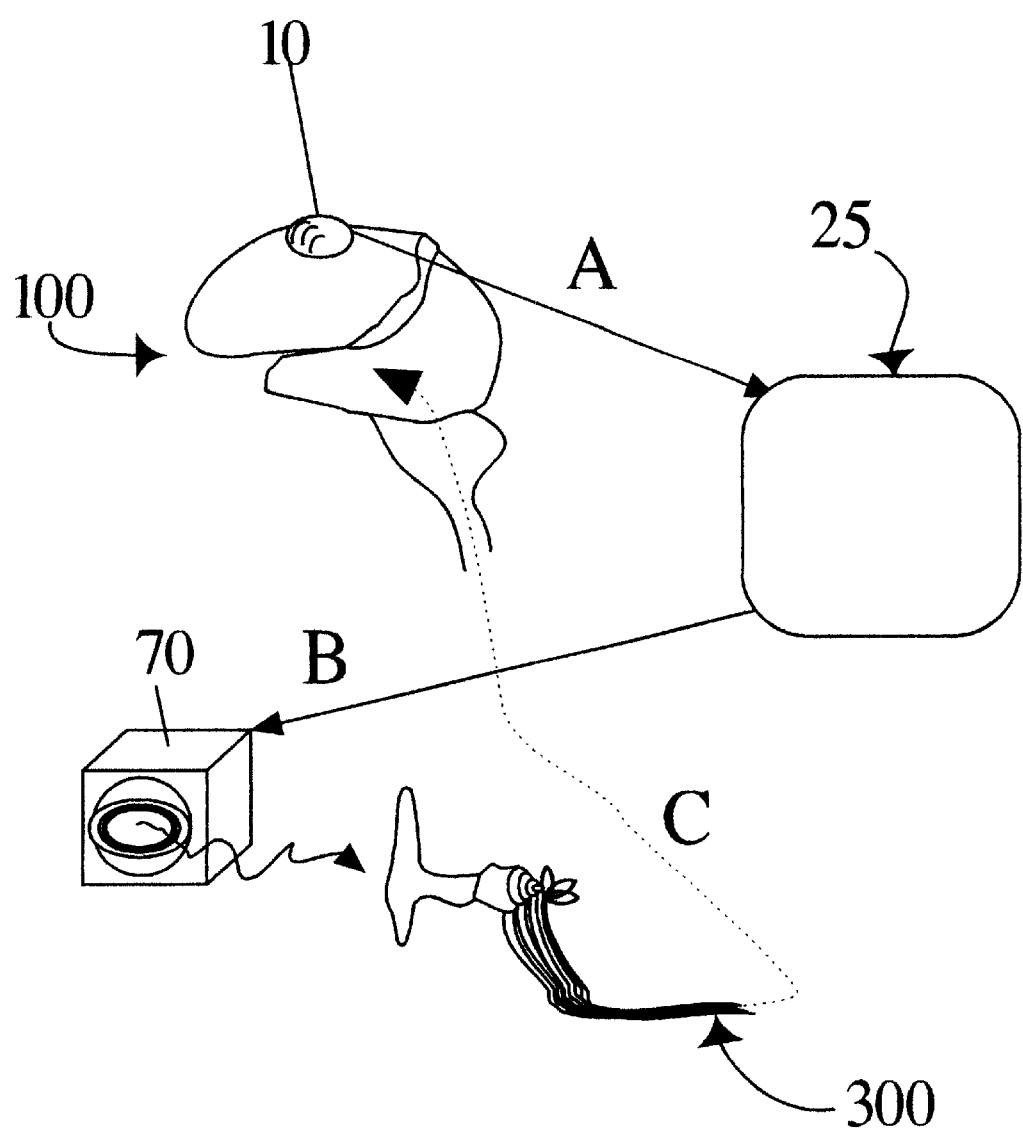
FIG. 6 schematically illustrates the monitoring of a brain and the stimulating of a vestibulocochlear nerve via audio signals going to an ear.

FIG. 6 illustrates a monitored brain causing a signal generator to send audio signals to an ear, which causes neuro-impulses to travel in defined pathways to the brain. Monitoringelectrode(10) picks up brain activation and sends signal(A) to controller means(25), whereupon on determining an abnormal brain activation occurred, signal(B) is sent to audio-generator(70) which sends out audio signals which the ear can ascertain. Then through the normal body mechanisms, the eighth cranial nerve excitation produces neuro-signals to travel to the brain.

Figure 7:
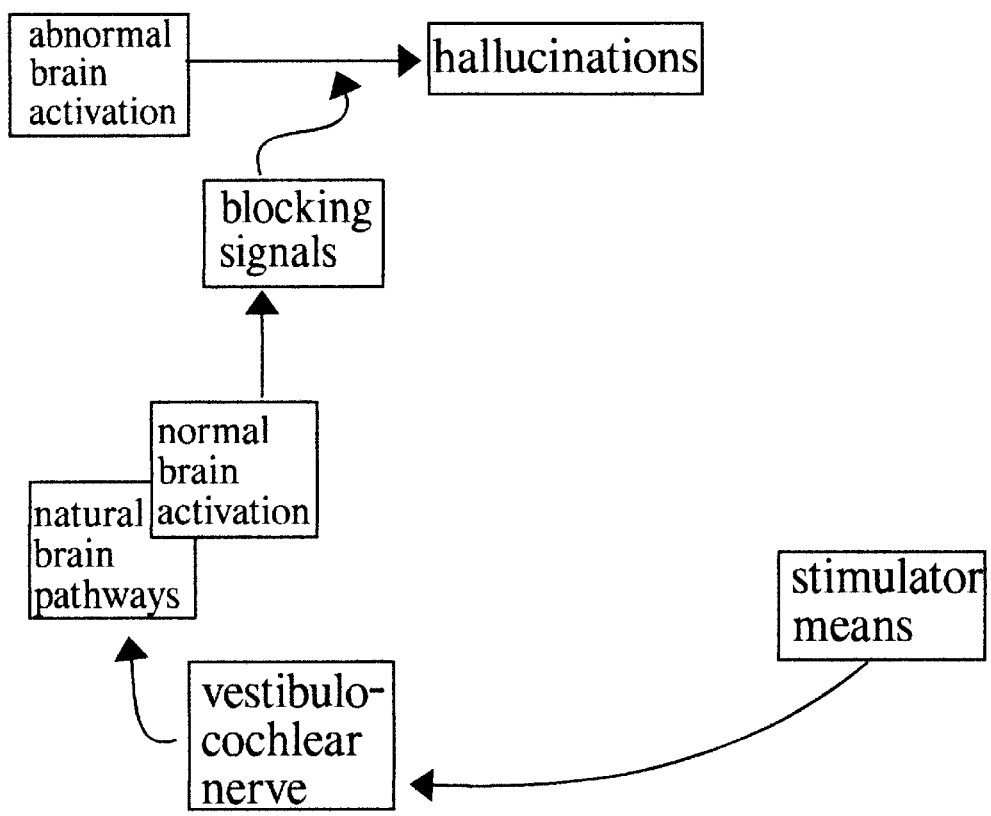
FIG. 7 is a block diagram of the method and apparatus of the present invention, wherein stimulation of a vestibulocochlear nerve causes normal brain activation signals that block abnormal brain activation (hallucinations).

FIG. 7 is a block diagram illustrating the method and apparatus of the present invention. A stimulator means causes vestibulocochlear nerve excitation through which natural brain pathways cause normal brain activation which in turn produces blocking signals. The blocking signals block abnormal brain activation (hallucinations).

Figure 8:
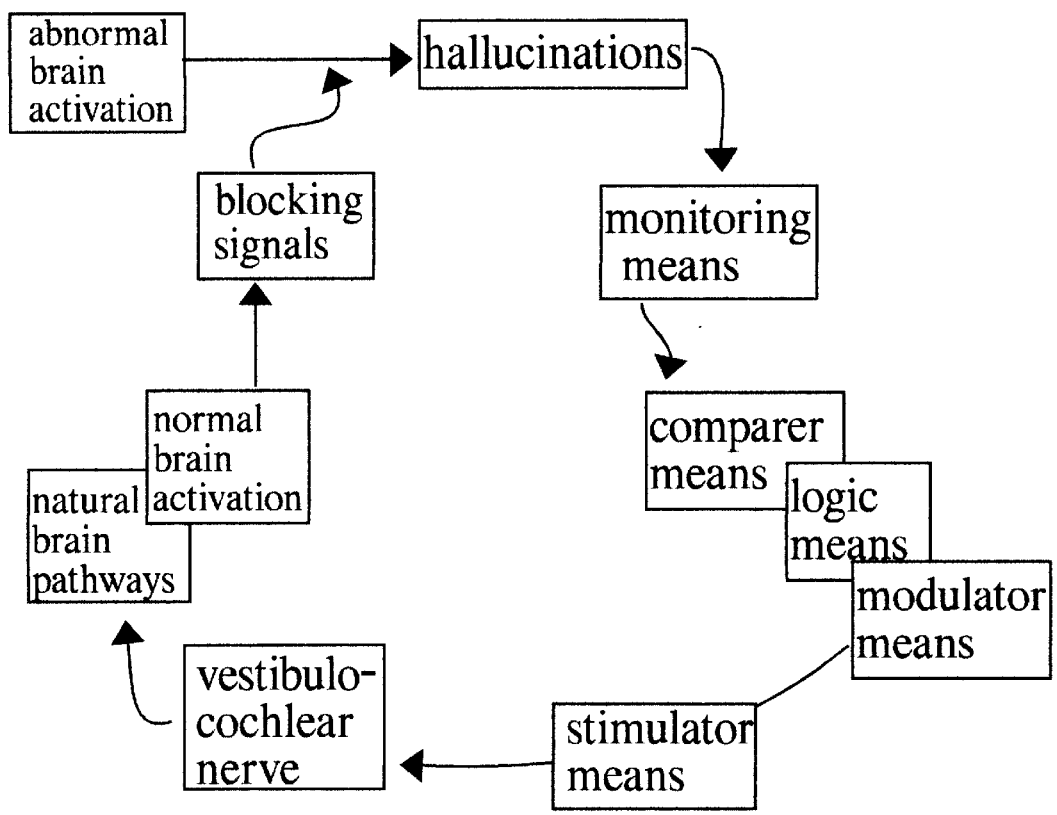
FIG. 8 is a block diagram of the method and apparatus of the present invention, wherein monitoring of brain for abnormal activation causes stimulation of a vestibulocochlear nerve thereby causing normal brain activation signals that block abnormal brain activation causing hallucinations.

FIG. 8 is a block diagram illustrating the method and apparatus of the present invention. A monitored brain signal is compared to predetermined parameters and logically determines whether hallucinations are present If present, a modulated signal is sent via a signal generator to a vestibulocochlear nerve which causes excitation through which natural brain pathways cause normal brain activation which in turn produces blocking signals. The blocking signals block abnormal brain activation (hallucinations).

Figure 9:
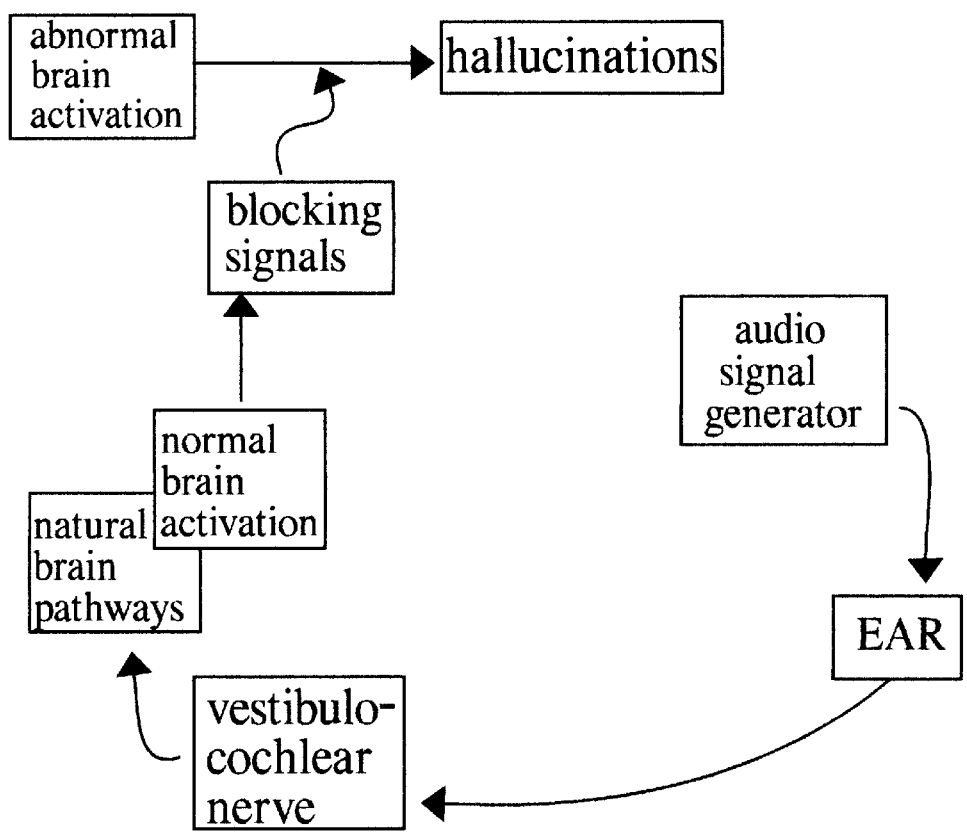
FIG. 9 is a block diagram of the method and apparatus of the present invention, wherein stimulation of a vestibulocochlear nerve via an ear causes normal brain activation signals that block abnormal brain activation causing hallucinations.

FIG. 9 is a block diagram illustrating the method and apparatus of the present invention. An audio generator sends a signal to an ear causing vestibulocochlear nerve excitation which causes neuro-signals to travel through natural pathways to the brain causing blocking signals. The blocking signals block abnormal brain activation (hallucinations).

Figure 10:
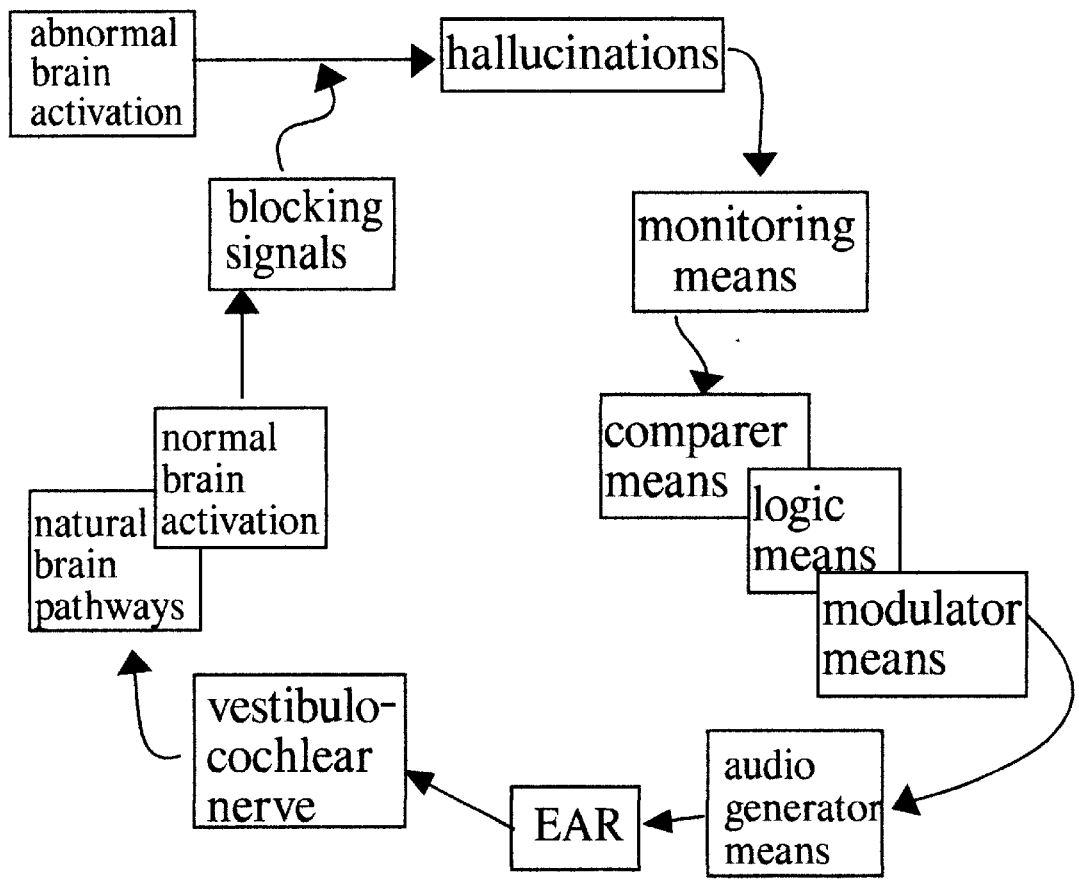
FIG. 10 is a block diagram of the method and apparatus of the present invention, wherein monitoring of brain for abnormal activation causes stimulation of a vestibulocochlear nerve via an ear thereby causing normal brain activation signals that block abnormal brain activation causing hallucinations.

FIG. 10 is a block diagram illustrating the method and apparatus of the present invention. A monitored brain signal is compared to predetermined parameters and logically determines whether hallucinations are present. If present, a modulated signal is sent to an audio generator means which sends a signal to an ear causing vestibulocochlear nerve excitation which causes neuro-signals to travel through natural pathways to the brain causing blocking signals. The blocking signals block abnormal brain activation (hallucinations).

Figures 11, 11A:
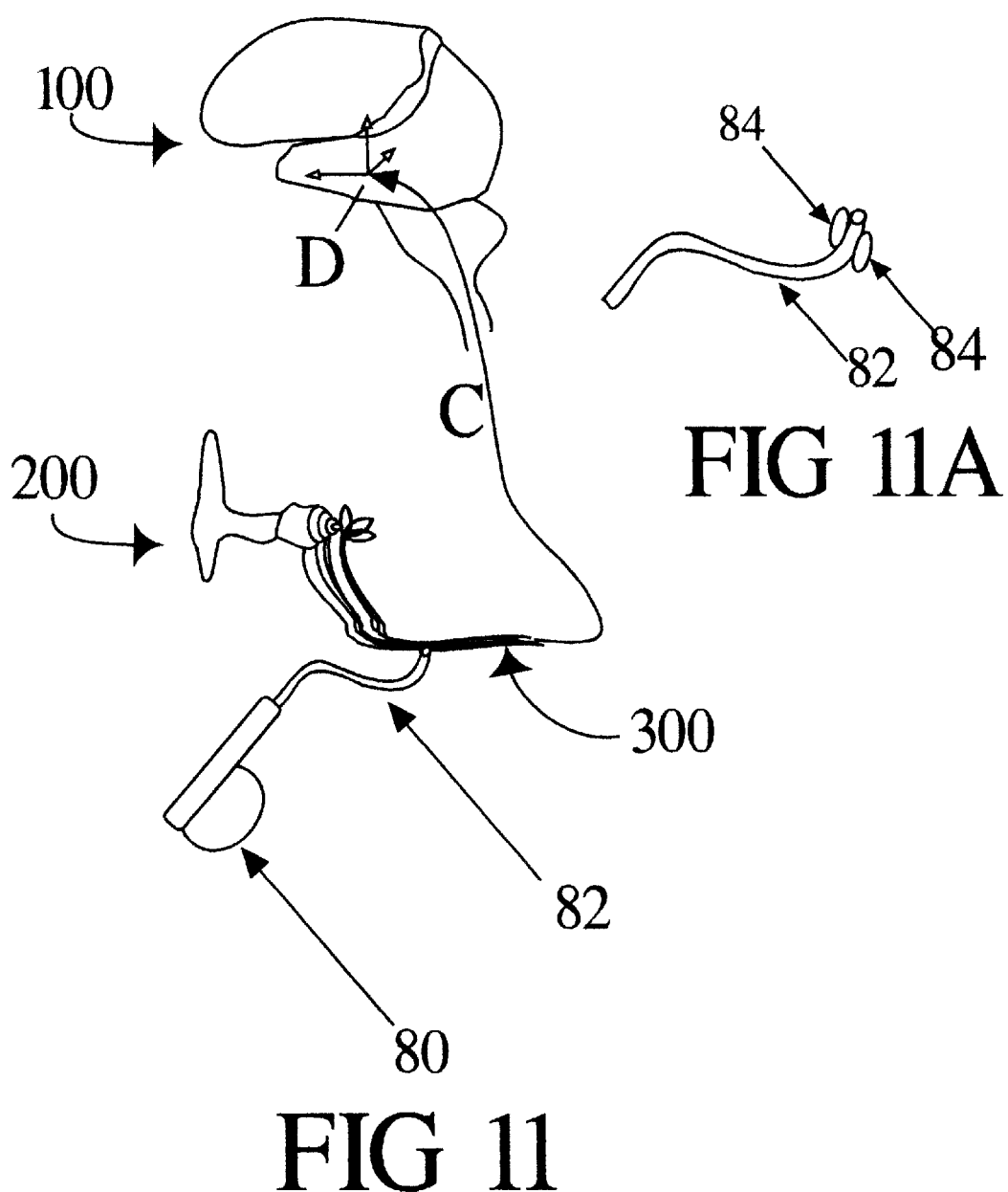
FIG. 11 schematically illustrates an infusion pump discharging a neuroactivating chemical to a eighth cranial nerve.
FIG. 11A schematically illustrates an infusion pump having a catheter comprising electrodes.

FIG. 11 illustrates an infusion pump(80) having a catheter (82) placed onto an eighth cranial nerve. In operation, the infusion pump discharges a neuroactivating chemical or drug onto the nerve, which causes neuro-impulses(C) to travel to the brain whereupon brain activation(D) occurs. FIG. 11A illustrates an infusion pump having a catheter(82) comprising electrodes(84) for combining the electrical stimulation with drug dosing.

As stated, neuro-impulses travel from the vestibulocochlear nerve to the brain through defined pathways and then spread to (activate) other regions of the brain. Any method of stimulating the eighth cranial nerve and its components may be useful. For example, infusing one or more drugs or chemicals having neuroactivation properties into or around the eighth cranial nerve will produce brain activation. One such method is using a surgically implanted catheter with electrodes and infusion pump so that the discharge portion lies in or near at least one vestibulocochlear cranial nerve or cochlea or cochlear region of a user.

The instant invention provides for the treatment and control of auditory hallucinations. Accordingly, a signal generator(40) may be implanted into, or worn external to the patient's body. The signal generator generates a programmable electrical wave form for application to electrodes implanted on at least one of the vestibulocochlear nerves or cochlea or cochlear regions of the patient. Said wave form may be changed via a programming wand held over the region of the microcomputer-based pulse generator. The electrical signal may be applied continuously, periodically, or intermittently. Parameter values of the electrical signal include pulse width, output current, frequency, on time and off time, and may be programmed according to predetermined values. Generally, these parameters are amplitudes of 0.1 to 20 volts, pulse widths varying from 0.02 to 1.5 milliseconds, and repetition rates preferably varying from 2 to 2500 Hz. Usually, blocking is done in the range 50 to 2500 HZ whereas facilitation is in the range of 2 to 100 Hz.

The signal generator may selectively be activated manually by the patient in order that the user have the ability to consciously control his/her auditory hallucinations.

The instant invention may also provide for a signal to be generated in response to certain patterns in a patient's EEG signal. Suitable means to monitor a patient's EEG, as well as suitable signal levels, frequencies, amplitudes and voltages for the stimulating signal are described in U.S. Pat. No. 5,269,303, the entire disclosure of which is incorporated herein by reference.

U.S. Pat. Nos. 4,702,254, 4,867,164 and 5,025,807, 5,231,988, 5,299,569 are disclosed and are incorporated herein by reference. These patents teach the stimulation of the vagus nerve, rather than the vestibulocochlear nerve, but in all other respects these patents provide appropriate techniques and devices amenable to the practice of the instant invention.

Cochlear and middle ear implants as in U.S. Pat. Nos. 4,988,333 and 5,549,658 are described and the entire disclosure of which is incorporated herein by reference. These patents teach the stimulation of the cochlear, middle ears, and the vestibulocochlear nerve for hearing impairment, but in all other respects these two patents provide appropriate techniques and devices amenable to the practice of the instant invention.

Implantable electrodes and infusion pumps as in U.S. Pat. No. 5,975,085 issued to Rise, 1999 is described and the entire disclosure of which is incorporated herein by reference. This patent teaches appropriate stimulation techniques and devices amenable to the practice of the instant invention.

The present invention is for treating a specific entity, that of hallucinations; however, electrical stimulation as described may also affect other symptoms of other diseases, such as phobias, panic attacks, obsessive compulsions or depression or other psychiatric disorders. The present invention may be embodied in other specific forms without departing from the spirit or essential attributes thereof and, accordingly, reference should be made to the appended claims, rather than to the foregoing specification as indicating the scope of the invention.

I claim:

1. A method of treating, controlling, or preventing auditory hallucinations comprising the steps of:
   surgically implanting at least one electrode adapted to be affixed to at least one vestibulocochlear cranial nerve or cochlea or cochlear region of a user; and
   applying an electric stimulus to energize said electrode.

2. A method of claim 1 wherein said user controls said electric stimulus.

3. A method of claim 1 wherein said user does not control said electric stimulus.

4. A method of treating, controlling, or preventing auditory hallucinations comprising the steps of:
   monitoring brain electrical or chemical activity;
   comparing monitored activity to predetermined parameters;
   logically determining the presence of hallucinations;
   surgically implanting at least one electrode adjacent to at least one vestibulocochlear cranial nerve or cochlea or cochlear region of a user; and
   applying an electric stimulus to energize said electrode.

5. A method of claim 4 comprising the additional steps of:
   surgically implanting an electrical or chemical sensor within a skull or on or within a brain; and
   using said sensor for monitoring electrical or chemical changes.

6. A method of claim 4 comprising the additional steps of:
   modulating an electrical stimulus and applying the modulated stimulus to energize said electrode.

7. An apparatus for using method of claim 1 for treating, controlling or preventing auditory hallucinations of a user comprising:
   at least one electrode means adapted to be affixed to a user's vestibulocochlear nerve or to a cochlea or to a cochlear region;
   a signal generator operatively attached to and for energizing said at least one electrode.

8. An apparatus of claim 7 wherein said signal generator is adapted to be used internal to said user's body.

9. An apparatus of claim 7 wherein said signal generator is adapted to be used external to said user's body.

10. An apparatus of claim 7 wherein said signal generator is controllable by said user.

11. An apparatus of claim 7 wherein said signal generator is not controllable by said user.

12. An apparatus of claim 7 additionally comprising a monitoring means on a user's skull or within or on a user's brain for monitoring brain electrical or chemical changes; wherein said monitoring means is operatively attached to a controller means adapted to be used comprising:
   a comparer means for comparing monitored activity to predetermined parameters;
   a logic means for logically determining the presence of hallucinations;
   a stimulus modulating means for modulating an electric stimulus sent to said signal generator.

13. An apparatus of claim 12 wherein said monitoring means comprises one or more electrodes.

14. An apparatus of claim 12 wherein said monitoring means comprises one or more chemical sensors.

15. A method for treating, controlling or preventing auditory hallucinations of a user comprising the following steps:
   monitoring brain electrical or chemical activity;
   comparing monitored activity to predetermined parameters;
   logically determining the presence of hallucinations;
   applying electrical and sound waves to a user's ear for inducing vestibulocochlear cranial nerve excitation to block said hallucinations.

16. A method of claim 15 wherein said sound waves are audible.

17. A method of claim 15 wherein said sound waves are inaudible.

18. An apparatus for using the method of claim 15 for treating, controlling or preventing auditory hallucinations of a user comprising:
   a monitoring means for monitoring brain electrical or chemical activity;
   a comparer means operatively attached to said monitoring means for comparing monitored activity to predetermined parameters;
   a logic means operatively attached to said comparer means for logically determining if hallucinations are present;
   a sound wave generating means operatively attached to said logic means for producing sound waves;
   wherein said waves enter a user's ear by air or bone conduction thereby inducing vestibulocochlear cranial nerve excitation to block hallucinations.

19. An apparatus of claim 18 wherein said sound wave generating means produces audible sound.

20. An apparatus of claim 18 wherein said sound wave generating means produces inaudible sound.

21. A method of using one or more drugs having neuro-activation properties to therapeutically treat hallucinations by means of an implantable drug pump and a catheter having a proximal end coupled to the pump and a discharge portion for infusing therapeutic dosages of the one or more drugs, the method comprising the steps of:

surgically implanting the catheter so that the discharge portion lies in or near at least one vestibulocochlear cranial nerve or cochlea or cochlear region of a user;

surgically implanting at least one electrode adjacent to at lease one vestibulocochlear cranial nerve or cochlea or cochlear region of a user; applying an electric stimulus to energize said electrode; and operating the pump to discharge a predetermined dosage of the one or more drugs through the discharge portion of the catheter into the infusion site, whereby hallucinations are treated.

22. A method of claim 21 wherein said catheter is combined with one or more electrodes and comprises the additional step of applying an electric stimulus to energize said electrode.

23. An apparatus of claim 7 wherein said electrode is combined with a catheter coupled with an infusion pump, for discharging one or more drugs in or near at least one vestibulocochlear cranial nerve or cochlea or cochlear region to treat hallucinations.

* * * * *